United States Patent [19]

Lauer et al.

[11] 4,337,396
[45] Jun. 29, 1982

[54] METHOD FOR BITUMEN ANALYSIS AND APPARATUS THEREFOR

[75] Inventors: James L. Lauer, Ballston Lake; Vincent W. King; Keyser K. Lau, both of Troy, all of N.Y.

[73] Assignee: Suncor Inc., Toronto, Canada

[21] Appl. No.: 156,908

[22] Filed: Jun. 6, 1980

[51] Int. Cl.³ ............................ G01J 1/00; G01V 5/00
[52] U.S. Cl. .................................... 250/340; 250/255; 250/351
[58] Field of Search ............... 250/255, 338, 340, 341, 250/351, 353; 350/6.6, 275

[56] References Cited

U.S. PATENT DOCUMENTS

| | | |
|---|---|---|
| 3,539,807 | 11/1970 | Bickel. |
| 3,631,246 | 12/1971 | Defriez. |
| 3,783,284 | 1/1974 | McCormack ...................... 250/339 |
| 3,793,525 | 2/1974 | Burch et al. ....................... 250/351 |
| 3,899,213 | 8/1975 | Fantasia et al. ................... 250/301 |
| 4,109,522 | 8/1978 | Thompson ........................ 250/338 |
| 4,157,655 | 6/1979 | Campbell et al. ................. 73/12 |

OTHER PUBLICATIONS

"A Laser Eye in the Sky May Help Spot Polluters", Chemical Week, Jun. 13, 1979, pp. 29-30.

Primary Examiner—Alfred E. Smith
Assistant Examiner—Janice A. Howell
Attorney, Agent, or Firm—J. Edward Hess; Donald R. Johnson; Paul Lipsitz

[57] ABSTRACT

Sand containing bitumen and like materials containing organic matter is analyzed quantitatively for its hydrocarbon content by use of a remote infrared sensor. In a preferred embodiment the bitumen is on a conveyor to further processing and if found unacceptable for processing by the method of the invention, the sand is automatically diverted. The invention also embodies the apparatus used for the analysis.

17 Claims, 8 Drawing Figures

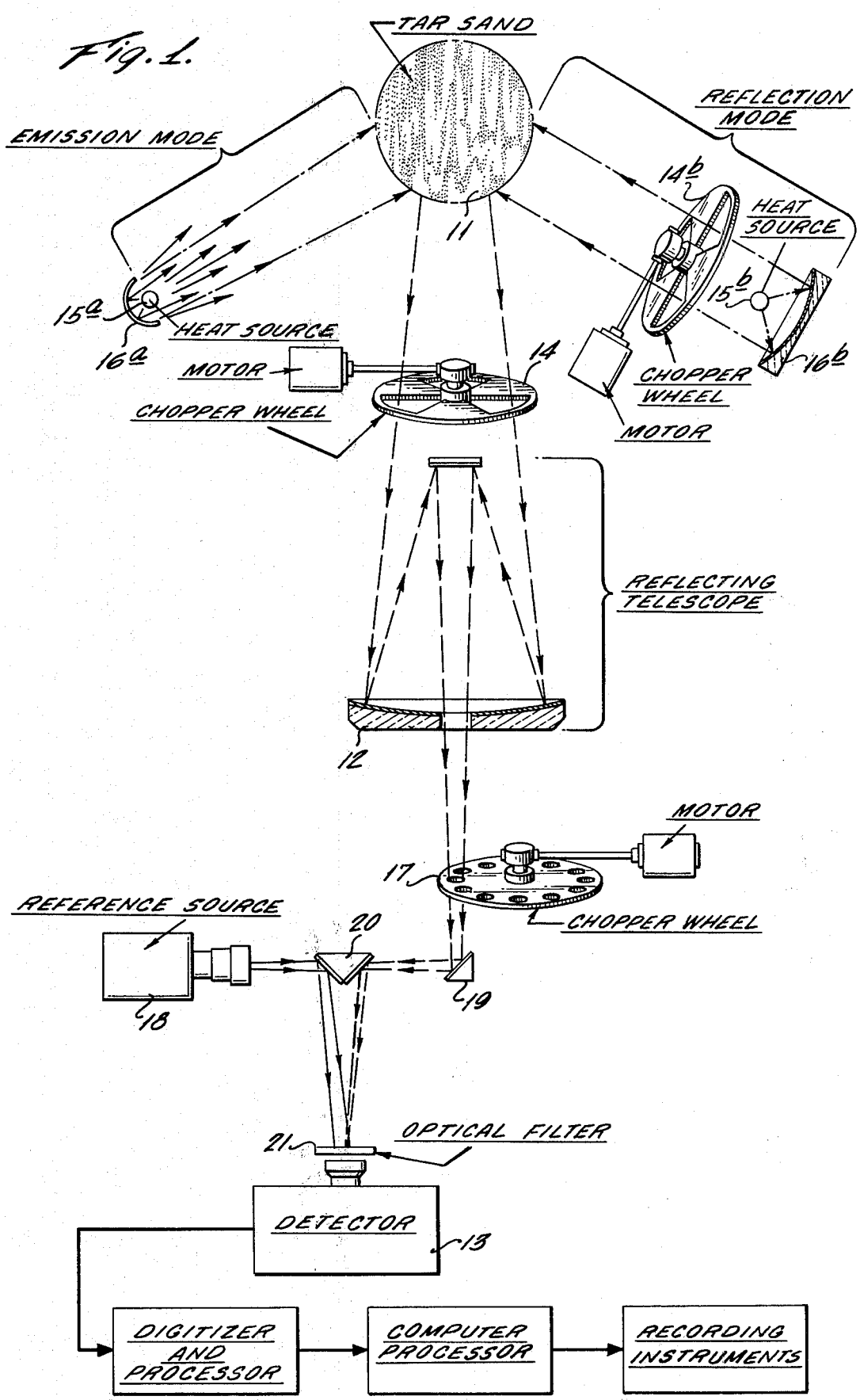

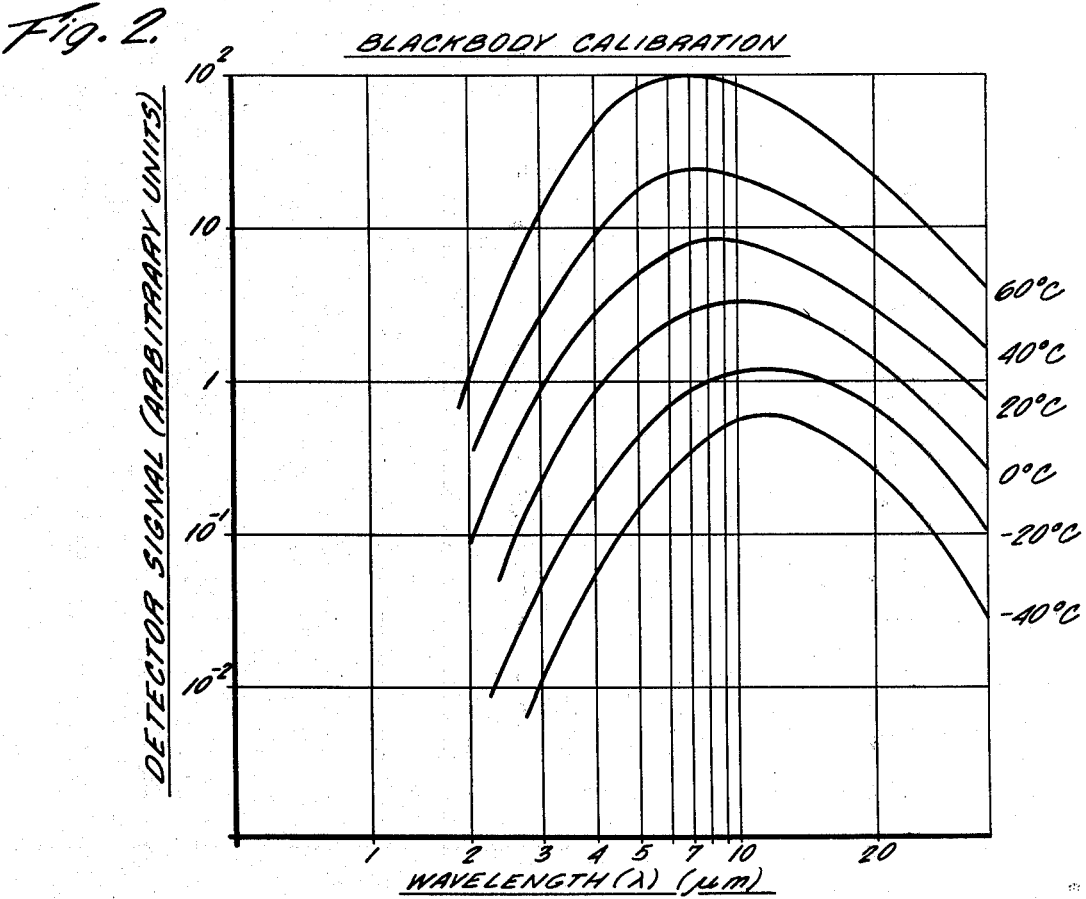
Fig. 2. BLACKBODY CALIBRATION
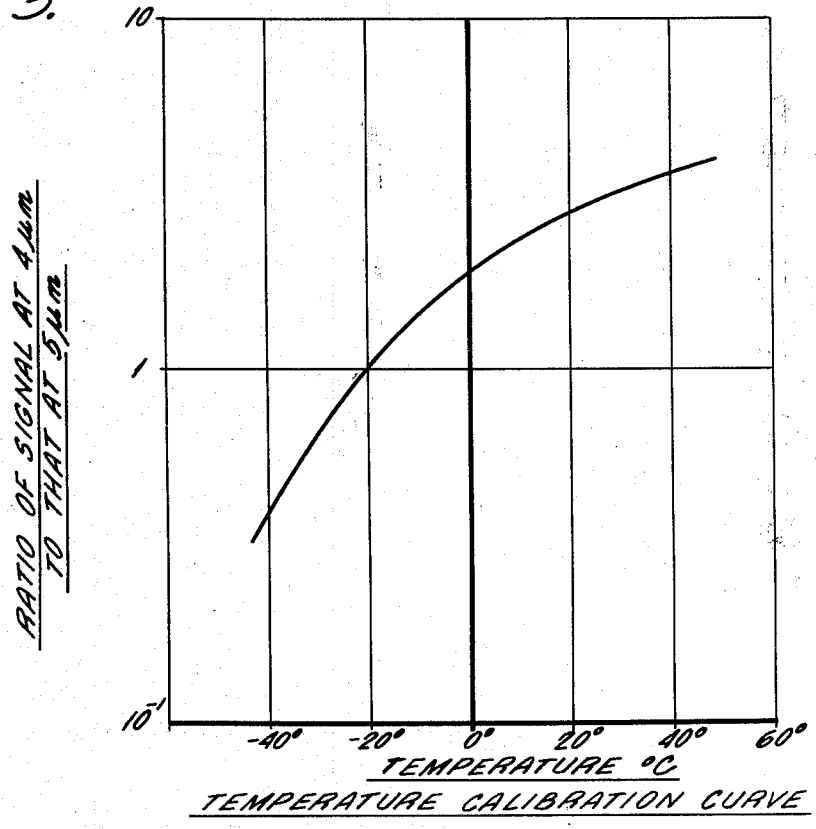
Fig. 3. TEMPERATURE CALIBRATION CURVE

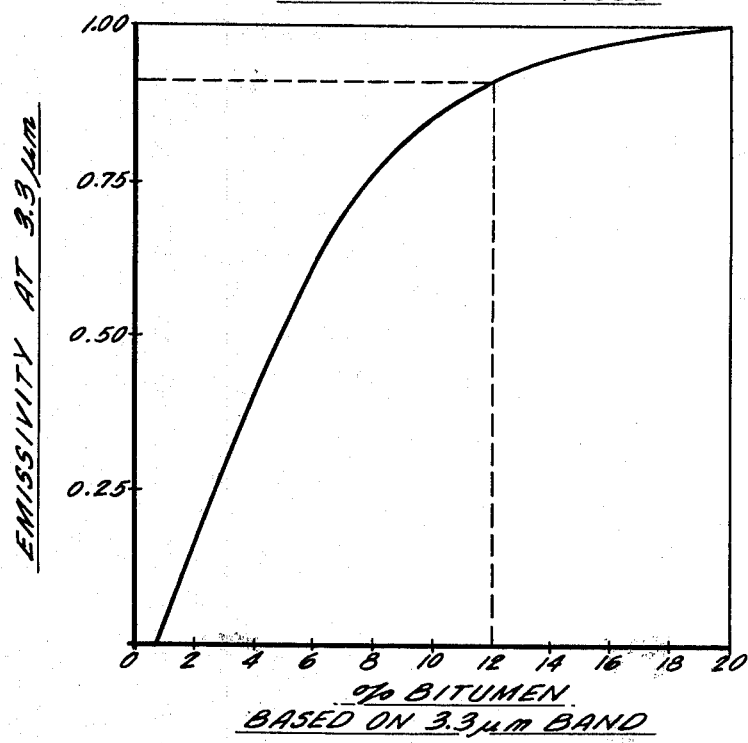
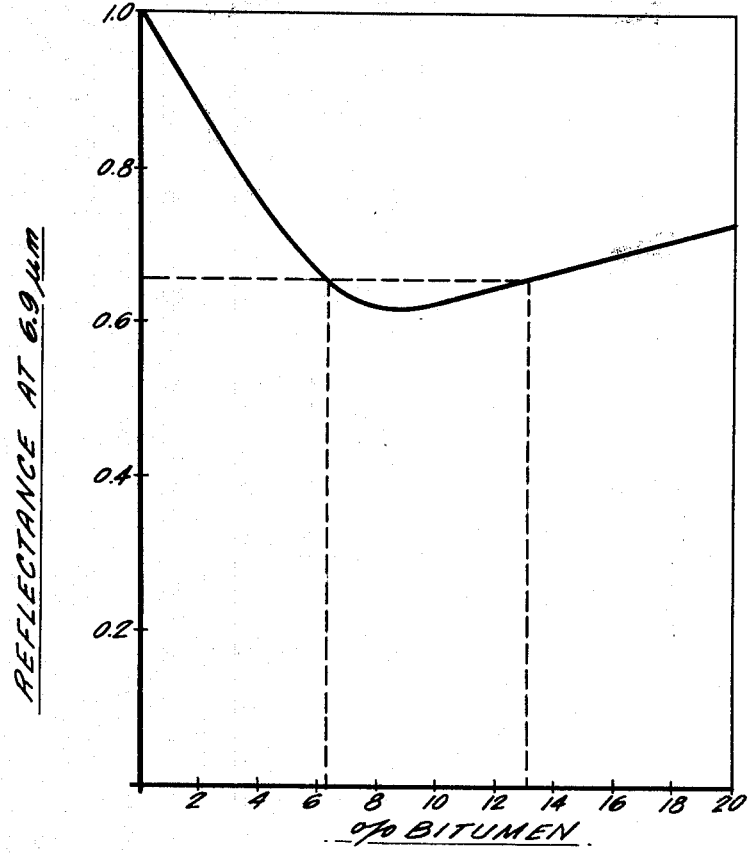

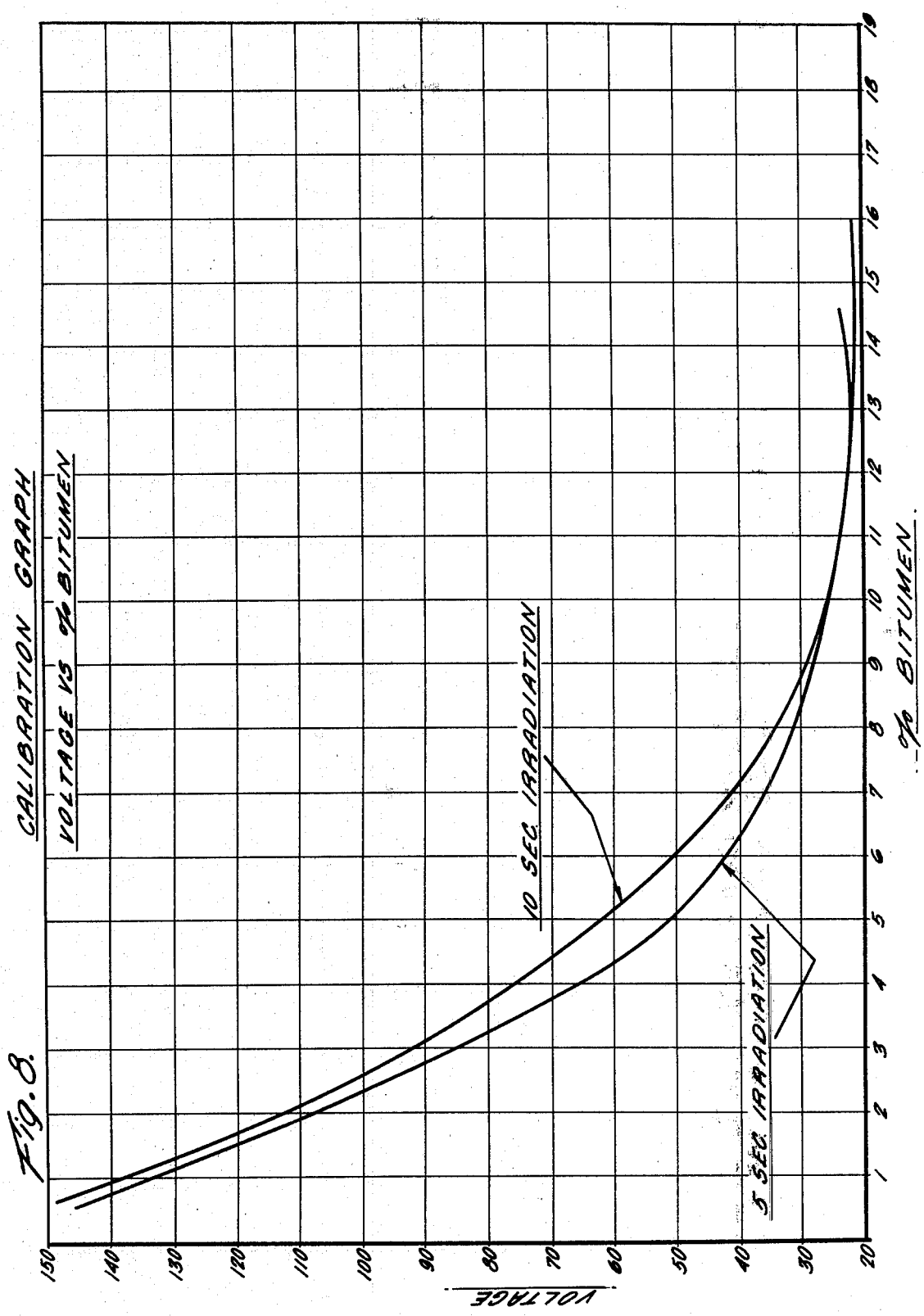

METHOD FOR BITUMEN ANALYSIS AND APPARATUS THEREFOR

This invention relates to analytical means for hydrocarbon analysis and is particularly concerned with bitumen in tar sands although the method is useful also for analysis of organic materials in other substrates such as shale, coal, lignite and the like. For illustration purposes the method will be discussed in terms of its application to tar sands. Tar sands are processed for the recovery of hydrocarbons by complex oil extracting and refining methods. After mining the tar sands they are conveyed, often by conveyer belt, to the processing units and it is important to know if the hydrocarbon content of the material is sufficient for proper processing in the equipment. This invention enables analysis of the tar sands to be remotely obtained.

It is known in the art to detect hydrocarbons by remote sensing. For example, U.S. Pat. No. 3,899,213 discloses remote identification of a marine oil spill by directing laser pulses onto the spill to cause fluorescence and measuring the fluorescence with appropriate detector devices. The method is sufficiently sensitive to enable identification of the type of oil and thus, possibly, the source of the spill. See also *Chemical Week*, June 13, 1979 pages 29–30 which describes the method.

In a similar method U.S. Pat. No. 3,032,655 describes the detection from an airplane of hydrocarbon leaks in a pipeline by measuring the infrared absorption of infrared from a solar source.

U.S. Pat. No. 3,961,246 employs taking an infrared spectrum with a spectrophotometer on a prepared sample of recovered, hydrocarbon-contaminated sylvite and using a calibration curve to measure the impurity concentration.

In U.S. Pat. No. 3,926,522 a far-infrared radiant meter is described for measuring the emissions of hydrocarbon and exotic fuels and flares in the 3 to 5 and 8 to 13 micron spectral region comprising a bandpass filter, pyroelectric detector, amplifier, demodulator filter and recorder. The system does not use a reference black body thereby eliminating reflective and refractive optics, but uses as a reference the source background and then introduces the target sample into the field of view.

U.S. Pat. No. 3,783,284 discloses a method of detecting petroleum products in a water area by reflected modulated infrared radiation.

U.S. Pat. No. 3,539,807 discloses a target identification method consisting of radiometric techniques using power difference signals at least two independent wavelengths to produce a temperature-independent target composition signal. The method assumes uniformity of composition and temperature for the target, though explicitly pointing out "that different materials can differ in temperature by as much as 40° F. as a result of uneven heating in the sunlight". The method uses a black body as a reference.

In the present invention, infrared emissions are employed to determine not merely the presence of hydrocarbons, but also the hydrocarbon content of bitumen such as tar sands. That is, the method is one which enables a quantitative analysis to be made. The method of the invention also permits the analysis to be made remotely while the tar sands are being conveyed to processing units and enables any tar sands below established standards for bitumen to be automatically prevented from entering the processing units. The present invention makes use of both temperature and infrared emissivity (or absorptivity) differences (emission mode) in such inhomogeneous materials and/or of reflectivity differences (reflectance mode) to obtain constituent analyses by infrared spectrophotometry. In the case of the tar sands, the emissivities (or absorptivities) and reflectivities are drastically different at certain infrared frequencies, because inorganic clays and organic bitumen have widely different infrared absorption spectra. Temperature differences between bitumen and clay can be as high as 30° C. during transportation on a conveyor belt due to the heat generated by the crushing of the rock and the flexing of the belt. However, these differences are not large enough to give the anaylsis the required accuracy. Therefore, in accord with the invention, a portion of the tar sand moving on the belt, or dropping from the belt into a hopper, is heated superficially by irradiation from an intense heat source to increase the temperature difference. Alternatively the radiation which is diffusely reflected by the tar sand from an intense heat source can be analyzed, the reflectance being complementary to the emittance. Emittance and reflectance, being complementary measurements, can be combined to provide a more accurate analysis, although either can be used separately with the electronic measuring arrangement described below.

FIG. 1 is a schematic drawing of the apparatus used in the method of the invention.

FIG. 2 is a black body calibration curve.

FIG. 3 is a temperature calibration curve.

FIG. 6 is a calibration curve for bitumen content in an emission mode.

FIG. 7 is a calibration curve for bitumen content in a reflectance mode.

FIG. 8 is an empirical calibration curve for bitumen analysis.

Figure 4:
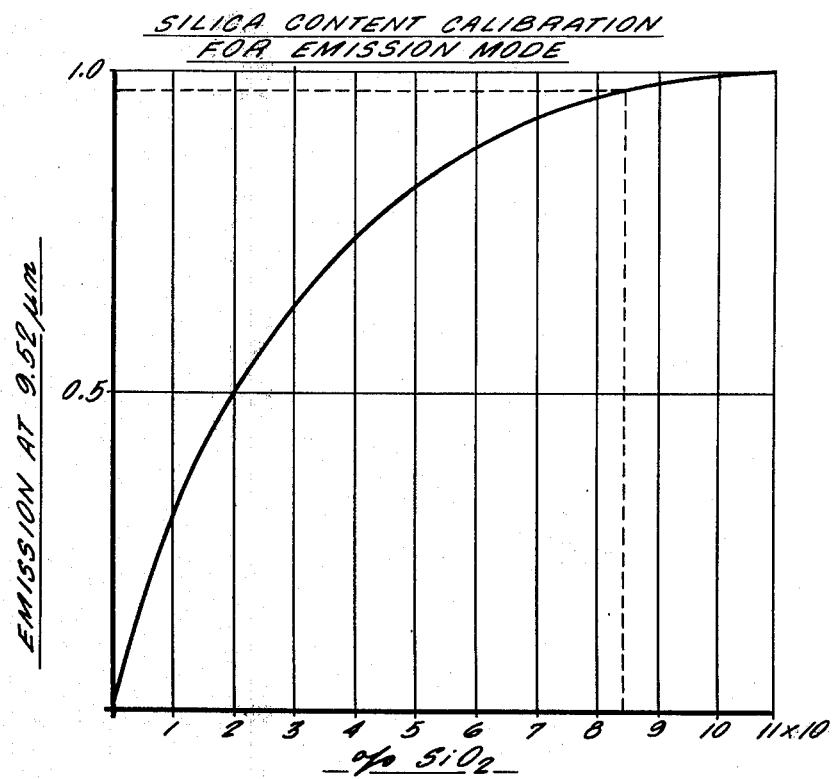
FIG. 4 is a calibration curve for silica content in an emission mode.

Referring to FIG. 1, it is seen that infrared radiation from tar sand 11, depicted as in flight while dropping from a conveyor belt to a storage bin in the processing plant, is focussed by appropriate optics (e.g., a telescopic mirror and transfer optics shown generally as 12) through an optical filter 21 onto the infrared-sensitive surface of a detector 13. The optical filters used will be those which will pass those wave lengths characteristic of the spectral radiance of the organic material. Even though care is taken to prevent extraneous radiation from falling onto the detector, much of the discrimination between source (the tar sand target) and extraneous signals must be done by one or more choppers 14 (interrupters of radiation) and amplifiers (not shown) phase-locked to their frequency. In the arrangement of FIG. 1, a rotating wheel containing a number of triangular openings (chopper 14) is placed very close to the moving sand, between telescope and sand to modulate the radiation. In this case, the detector 13 is kept at a constant temperature below that of the sand. The chopper wheel is blackened, to reduce to a minimum the possibility of extraneous signals being reflected into the detector at the chopper frequency and thus being detected. Another chopper 17 having a number of circular holes equidistant from the axis of rotation and from one another rotates in phase with and at the same angular speed as chopper 14 and is located near the detector. A pair of prisms (19 and 20) directs the target signal to the detector and a signal from a reference source 18 is directed through prism 20 alternatingly with the target signal to the detector 13. Alternatively and not shown, the prisms 19 and 20 may be eiliminated if chopper 17 is placed at an angle of 45° with the optic axis near the detector 13. In such a case all of the surfaces, except those of the reference, seen by the reflecting surfaces of chopper 17 are aluminized, or placed behind reflecting baffles to avoid reference signal contamination and to prevent detection of spurious radiation along the path from 14 to 17. In another alternative arrangement, chopper 17 may be placed between optical filter 21 and the detector 13.

The use of at least two synchronous choppers, one near the target and one near the detector, is important for the successful operation of the analyzer, especially in the emission mode of operation because the effectiveness of the system is very much lower with a single chopper as is used in the prior art systems. Chopper 17 alone would work when unwanted sources of radiation could be shielded, but this would be difficult or impossible in field use. Chopper 14 renders potentially interfering sources along the distance between and detectors innocuous, because their radiation is not chopped.

It will be understood that the heat source 15b and chopper 14b may be replaced with pulsed laser which will act in an equivalent manner to a chopped heat source. Use of a pulsed laser is, in fact, a preferred method because the laser has intense, collimated radiation which can act over a long distance from the tar sands being analyzed. Similarly, the heat source 15a may be replaced by a continuous laser for operation in the emission mode.

As indicated, a strong source of infrared radiation 15a is reflected from a mirror 16a to increase the sensitivity of the method. The effect of heating the target is to increase its surface temperature; and the bitumen temperature, because of the greater infrared absorptivity by bitumen in much of the infrared region, will thereby be somewhat higher than the sand temperature. In the configuration just described, the system is operating in the emission mode. However, when the location of chopper 14 is moved to a position in front of the infrared source (14b and 15b) whose radiation is strongly collimated as shown by the dashed lines penetrating chopper 14b in FIG. 1, the system is then operating in the reflecting mode. At wavelengths whose radiation is strongly absorbed by the hydrocarbons constituting the bitumen, the radiation detected is mostly originating from the sand, and vice-versa. In the reflection mode, the discrimination against background contamination is superior to that of the emission mode, but the signal is weaker. When operating in the reflection mode the electronics are usually modified so that the heat source itself is used as reference. For instance, a tunable dye laser may be used as both source 15 and reference 18, and a photocell next to the laser is then used to monitor its intensity and it is this photcell's current that is introduced into the detector circuitry alternatingly with the target signal.

It will be understood that when operating in the emission mode, some reflectance will be obtained and vice versa since complete separation of reflectance and emission cannot be readily achieved, nor is it necessary to do so.

Sources for heating a small portion of the tar sand in motion to the processing plant can be any one of several; e.g. an electric spectroscopic graphite (carbon) arc provided with a good parabolic mirror for collimation, or a blob of tungsten tool steel heated by a blue oxy-acetylene flame. Glass-enclosed arc lamps are not suitable because of the absorption of much of the infrared by glass. However, an infrared diode or tunable dye laser (which does not need an infrared filter) is an excellent source. A carbon dioxide laser is also an excellent heat source. The time of irradation of the sample may vary from about 0.1 to about 10 seconds or more, and if the tar sand is moving the irradiation time will depend upon its speed. In general with tar sands on a moving belt the irradiation time will be about 0.1 to about 1.0 seconds.

As indicated in this reflective laser technique, preferably an infrared tunable laser is used to irradiate the sample and the reflective infrared radiation is detected as described above. It is preferable to use the laser itself as the reference source for the sample as this will significantly increase discrimination by reducing noise since the effective temperature of the laser is enormously high. By use of the tunable laser, the system lends itself to a wide variety of materials for detection.

The preferred detector will be highly sensitive over a wide range of infrared frequencies. If it is a pyroelectric detector, such as a lithium tantalate, or a pneumatic detector, such as a Golay cell, it is almost uniformly sensitive over the entire common infrared range. If it is a solid state detector, such as mercury-cadmium-telluride, operated at liquid nitrogen temperature, corrections must be made for its frequency-dependent sensitivity.

The detector sees alternatingly the target 11 and the reference 18. The reference in certain prior art systems for radiometric analysis (e.g. U.S. Pat. No. 3,539,807 discussed above) is a so-called "black body" which may be a cylindrical or conical center hole in a substantial solid metal block. In the method of this invention, a "black body" may be used for calibration, but not as a reference. The reference used in the system may be a sample essentially the same as the target; e.g. a bitumen sample, since this gives better discrimination than a blackbody. Alternatively, as explained above, a turnable laser may be used as a reference source. The reference tar sand sample should be as similar as possible to that of the material being analyzed; that is, the sample and reference source should be balanced as to radiant power. In one version of the analyzer a thermoelectric (Peltier effect) cooler may be used with the reference. The lock-in amplifier is tied to the reference and furnishes a signal representing the difference in radiant power between target and reference. This signal is then digitized, stored on a magnetic storage device, processed by a microprocessor or minicomputer and fed to a recording device as depicted in FIG. 1.

As indicated, an optical filter 21 is inserted into the optical path in front of the detector as shown in FIG. 1. Such filters are mounted on slides which are used for the tar sand analyses. They have a transmission bandpass, centered about (i) 1.050 cm$^{-1}$, (ii) 1,450 cm$^{-1}$, (iii) 2,000 cm$^{-1}$, (iv) 2,500 cm$^{-1}$, and (v) 3,030 cm$^{-1}$. Such selection is based on the following: (i) the 1,050 cm$^{-1}$ band is most characteristic of the silica; the (ii) 1,450 cm$^{-1}$, and (iii) 3,030 cm$^{-1}$ band are characteristic of hydrocarbons in bitumen, the latter of aromatics, and the (iv) 2,000 cm$^{-1}$, and (v) 2,500 cm$^{-1}$ regions are used as two reference points on the continuous blackbody background. At all these wavelengths the difference of target and reference signals is obtained.

The primary data processing procedure in the emission mode may be done by the following three steps:

(1) Signals at 2,000 cm$^{-1}$ and 2,500 cm$^{-1}$, or equivalently at 4 and 5 μm wavelengths, are substituted into Planck's equation, $$P(\lambda, T) = \epsilon(\lambda) \frac{2\pi c^2 h}{\lambda^5 \left(e^{\frac{hc}{\lambda kT}} - 1\right)} \quad (1)$$

to find $\epsilon(\lambda)$, the emissivity and T, the absolute temperature. Experience has shown that $\epsilon(\lambda)$ is effectively the same at both 4 and 5 μm wavelengths, so that a kind of average temperature of the target can be established. This temperature is predominantly that of the sand's surface which in almost all instances constitutes more than 85% of the tar sand.

In Equation (1) the symbols not yet referred to are;
c, the velocity of light, $3.00 \times 10^{10}$ cm.sec.$^{-1}$,
h, Planck's constant, $6.55 \times 10^{-27}$ erg.sec., and
k, Boltzmann's constant, $1.37 \times 10^{-16}$ erg,deg.$^{-1}$. (2) Signals at 1.050 cm$^1$, ($\lambda = 9.52$ μm) are substituted in Equation (1) to determine an effecitve $\epsilon(\lambda 9.52$ μm) at the temperature previously calculated. Using a calibration procedure described below, this $\epsilon(\lambda = 9.52$ μm) can then be applied to find the surface concentration of silica.

(3) Signals at 1,450 cm$^{-1}$, ($\lambda = 6.90$ μm) and at 3,030 cm$^{-1}$, ($\lambda = 3.3$ μm) are substituted in Equation (1) to calculate the ratio $\epsilon(\lambda = 6.90$ μm$)/\epsilon(\lambda = 3.3$ μm), from which the bitumen content can be determined with the help of a calibration. Inspection of Equation (1) will show that this ratio is independent of the bitumen temperature, which may be different from that of the clay. However, independent calibrations for $\epsilon(\lambda = 6.90$ μm) and $\epsilon(\lambda = 3.3$ μm) are also available for known temperatures, making it possible to check for temperature differences between clay and bitumen temperatures.

In the reflection mode the primary data processing procedures involve only calibrations at respective wavelengths or frequencies since temperature corrections are usually unnecessary, that is, the calculating procedures are entirely empirical. However, the calibrations are available at different temperatures and, if necessary, the principal temperature may be found as shown under (1), using the emission mode. For this purpose chopper 14 is transferred to position 14b as discussed previously.

In the usual embodiment of this invention the amplified signals are recorded, one per second or more often, summed, and stored on a suitable memory device. Usually many thousands of data points are thus summed or averaged over a period of several minutes. Then concentrations are calculated by microprocessors by means of empirical equations representing the calibration curves obtained previously. The results are then displayed on a cathode ray screen or on printed paper tape. The plane operator can use these results to divert the tar sand or pass it to further processing as it is carried on moving belts toward the bitumen extracting unit. Thus tar sands on a moving belt may be controlled to pass into extraction units only when of sufficiently high hydrocarbon content. If, however, the hydrocarbon content is below a given level, a diverter blade can be activated to divert the target material for special handling; e.g. to transfer the tar sands to a second moving belt for storage. Alternatively, the diversion can be done entirely automatically, without an operator's help.

In either case, a permanent record of the composition, and how it was handled at a particular time may be provided on printed paper tape.

EXAMPLES

I. Calibration

The wave lengths or signals given in the following discussion refer to the centers of the band pass transmitted by the filters.

(i) The "standard blackbody" reference sources may be constructed or purchased as standard parts. The detector signals at the five frequencies referred to above are noted for a number of temperatures over the range encountered in practice, i.e. for example, at $-40°$, $-20°$, $0°$, $20°$, $40°$ and $60°$ C. Curves plotted of detector signal (equivalent to spectral radiance) are plotted against wavelengths as shown in FIG. 2.) They are obtained by fitting the experimental values to Planck's equation (Equation 1) by standard least square techniques.

(ii) The ratio of spectral radiances, respectively of the signals at 4.0 and 5.0 μm is plotted against temperature from the above information. This information is shown in FIG. 3 which illustrates the resulting curve.

(iii) Curves of emissivity of mixtures of known bitumen/sand ratio versus composition are determined under actual field conditions. An example of such a curve at 9.52 μm, predominantly the silica band, is shown in FIG. 4. Similar curves are obtained for the bitumen bands at 6.9 μm (FIG. 7) and at 3.3 μm (FIG. 6).

Figure 5:
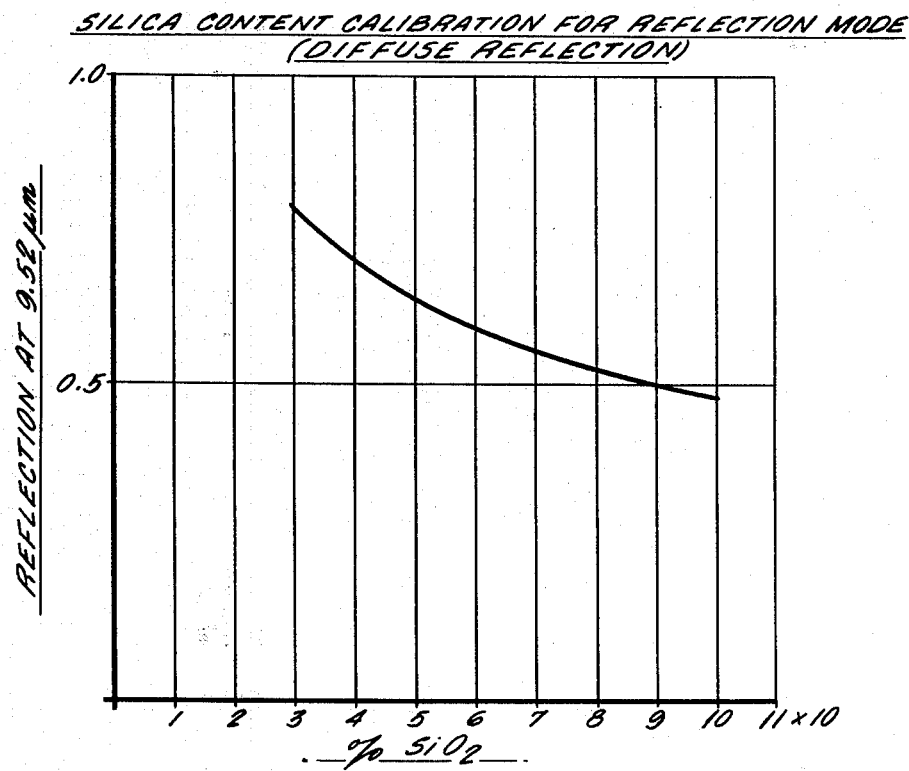
FIG. 5 is a calibration curve for silica content in a reflectance mode.

(iv) Similar silica content curves are plotted for diffuse reflectivity vs. composition at the same wavelengths as above. FIG. 5 shows such a curve for 9.52 μm.

II. Bitumen Analysis

Using the equipment and methods described above and as shown in FIG. 1, the bitumen in a tar sand is determined by the emission mode and by the reflection mode.

(A) Emission Mode

The data processing procedures described previously are followed making use of the calibration curves. The calibration curves are converted to empirical (power series) equations for digital data processing. More specifically:

(i) Signals at 4.0 and at 5.0 μm are ratioed at the "background temperature" obtained from FIG. 3. Knowing this temperature, the expected signals for an emissivity of unity (blackbody) are obtained from FIG. 2 at these two wavelengths. Dividing these into the actual signals give effective emissivities for these two wavelengths, which are always essentially equal.

(ii) Signals at 9.52 μm (the silica band) are divided by the expected blackbody signals (FIG. 2) for this wavelength at the above-determined temperature. The resulting emissivities are used with FIG. 4 to provide a silica concentration.

(iii) Signals at 6.9 and at 3.3 μm (the hydrocarbon bands) are divided by the expected signals for this temperature (FIG. 2). The resulting emissivities are used with the concentrations vs. emissivity curves (FIGS. 4 and 6) for these wavelengths and hydrocarbon concentrations are obtained that are somewhat different for the two wavelengths. The concentrations obtained for 3.3 μm shows more scatter than those obtained for 6.9 μm. This result indicates that the temperatures used with FIG. 2 are too low (signals weak) and on using a temperature for bitumen which is 20° C. higher than for the silica, nearly identical concentrations from the two wavelengths are obtained.

The concentrations determined in this sample are found to be 12% bitumen and 85% sand (as silica). The broken lines in the calibration charrts (FIGS. 4 and 6) show how the values are obtained.

(B) Reflection Mode

The analysis of the same sample by the reflection mode is easier, since only reflectivities are needed. This is performed with the help of the calibration curves of FIGS. 7 and 8. The reflection is both diffuse and specular, primarily in the case of bitumen. Specular reflectivity generally increases with increasing absorption of radiation, but diffuse reflectivity decreases. However, as the bitumen content increases, the regular (specular) reflection also becoms dominant, so that the reflectivity overall increases with bitumen content from a concentration of about 8% on. For silica (sand) the reflectivity always decreases at 9.52 μm. In order to pick out the proper analysis for bitumen the silica content of 84% from FIG. 7 must be considered since the broken horizontal line in FIG. 8 could lead one to conclude that the sample contained either 6 or 13% of bitumen.

Thus, since the sand plus bitumen content of the sample must total about 100% only the 13% bitumen value is conceivable. Using the calibrations of FIG. 5 and a similar one for 6.90 μm the value of 13% and 84% are obtained respectively for bitumen and silica.

(C) Combined Modes

It has been found that, in general, greater sensitivities can be obtained by determining bitumen by emission and silica by reflection and since the electronic system allows switching of modes in any desirable way this provides a simple means for a very suitable system. The choise cannot be made for a general case, since particle sizes of tar sands can differ which affect the distributions of specular and diffuse reflections, but, as indicated, it has been found best to determine bitumen by emission.

Preferred Empirical Method

In a preferred empirical technique for analysis, the sample being analyzed is used as a reference and readings from the detector in volts read on a digital voltmeter are taken at 5.1 μm. At this wave length neither the sand nor the bitumen has significant emission or absorption. Therefore the sand behave as a gray body and will absorb or emit depending only upon its temperature and the concentration of bitumen in sand does not affect the emission reading. This reading is then employed as a reference signal and is used to represent the temperature of the sand-bitumen mixture. Emission readings at other wave lengths over the desired range (say 4.03, 2.59–3.15, 3.75–4.28 μm) are then referred (i.e. ratioed) to the 5.1 μm reading by the electronic circuitry in order to eliminate the effect of temperature and the results are plotted against known bitumen concentration in order to obtain a calibration. FIG. 8 is a typical calibration curve showing volts vs. percent concentration of bitumen when readings are taken on the sample at 5 seconds and 10 seconds irradiation time. Using this calibration curve, the voltages obtained at 5.1 μm from unknown tar sands are used to obtain the bitumen concentration. The results obtained in this way have been found to be accurate to better than one-half of one percent.

A main advantage of this invention is the rapidity of the analysis, which ranges from seconds to minutes. Since very large amounts of the tar sands are moved, the recognition of high or low bitumen content for appropriate processingis of a considerable economic importance, and represents a significant advance in the art.

The invention claimed is:

1. A method for the quantitative analysis of hydrocarbons in tar sands, coal, shale or similar materials wherein said material is heated and the thermal radiation from said material is passed through at least two synchronous radiation choppers and through a band pass optical filter characteristic of the spectral radiance of the hydrocarbon in the target material to radiation detector means, a first chopper being close to said material being analyzed and the radiation passing through said first chopper being focused to pass through a second chopper rotating in phase and at the same angular speed as said first chopper, and radiation from a reference source which is a material essentially the same as the target material or a tunable laser being directed alternately with the radiation from said material to said detector, the concentration of hydrocarbon in said material being determined by comparison with calibration curves of the detected radiation and percent concentrations.

2. A method for the quantitative analysis of bitumen in tar sand in the field wherein said tar sand is heated and the thermal radiation from said tar sand is passed through two synchronous radiation choppers and through a band pass optical filter characteristic of the spectral radiance of the bitumen in the target material to radiation detector means, a first chopper being close to said sample being analyzed and the radiation passing through said first chopper being focused to pass through a second chopper rotating in phase and at the same angular speed as said first chopper, and radiation from a reference source which is a material essentially the same as the target material or a tunable laser being directed alternately with the radiation from said tar sand to said detector, the concentration of bitumen in said tar sand being determined by comparison with calibration curves of the detected radiation and percent concentrations.

3. The method of claim 2 wherein the radiation from the tar sand target is essentially emissive radiation.

4. The method of claim 2 wherein the radiation from the tar sand target is essentially reflective radiation.

5. The method of claim 1 wherein the reference material is essentially the same as the target material.

6. The method of claim 2 wherein the reference source is essentially the same as the target material.

7. The method of claim 2 wherein the reference source is tar sand.

8. The method of claim 1 wherein a tunable laser is used as the heat source and the reference source.

9. The method of claim 2 wherein a pulsed laser is used both as a heat source and as the first chopper.

10. The method of claim 2 wherein a continuous laser is used as the heat source.

11. The method of claim 2 wherein a tunable laser is used as the heat source and the reference source.

12. The method of claim 1 wherein means responsive to a predetermined signal characteristic diverts said target hydrocarbon for special handling.

13. The method of claim 12 wherein the target hydrocarbon is tar sands.

14. An apparatus for the analysis of hydrocarbons in target tar sands, coal, shale and like material comprising means to heat the target material, means to focus radiant energy from said heated target through a first and a second chopper, an optical filter characteristic of the spectral radiance of the hydrocarbon in the target material, a source of reference radiation, and a detector to receive said radiation from said target material and said reference, said first chopper being near said target material and said second chopper being in phase with said first chopper, whereby radiation from said target material and said reference alternately passes through said choppers and is detected by said detector.

15. The apparatus of claim 14 wherein the heating means is a continuous laser.

16. The apparatus of claim 14 wherein a tunable laser is used as the heating means and the reference source.

17. The apparatus of claim 14 in combination with diverting means which is responsive to a predetermined signal whereby the target hydrocarbon is diverted for special handling.

* * * * *